United States Patent [19]

Wyatt

[11] 4,251,810
[45] Feb. 17, 1981

[54] APPARATUS FOR AND METHODS OF REMOTELY MONITORING OUTPUTS OF GEIGER-MUELLER TUBES

[75] Inventor: David M. Wyatt, Arlington Heights, Ill.

[73] Assignee: Kay-Ray, Inc., Arlington Heights, Ill.

[21] Appl. No.: 910,910

[22] Filed: May 30, 1978

[51] Int. Cl.² .............................................. G01N 23/12
[52] U.S. Cl. .................................... 340/612; 340/517; 340/617; 250/357
[58] Field of Search ............... 340/517, 533, 595, 596, 340/600, 612, 617; 250/357, 388

[56] References Cited

U.S. PATENT DOCUMENTS

| 2,323,128 | 6/1943 | Hare ...................................... 250/357 |
| 2,713,124 | 7/1955 | Graham ................................ 250/357 |
| 2,972,050 | 2/1961 | Allen ..................................... 250/357 |
| 3,389,250 | 6/1968 | Clemens ............................... 250/357 |
| 3,560,801 | 2/1971 | McCarther ........................... 361/170 |
| 3,594,575 | 7/1971 | Shoemaker .......................... 250/357 |
| 3,668,392 | 6/1972 | Bajek et al. .......................... 250/357 |
| 3,944,830 | 3/1976 | Dissing ................................ 250/358 |

Primary Examiner—Alvin H. Waring
Attorney, Agent, or Firm—Kinney, Lange, Braddock, Westman and Fairbairn

[57] ABSTRACT

Apparatus for and methods of remotely monitoring outputs of Geiger-Mueller tubes including cables for connecting individual Geiger-Mueller tubes to a central monitoring station wherein electronics for sensing the output of each tube is located at the central station rather than juxtaposed with each tube. The electronics are used to trigger individual alarms and a general alarm whenever radiation levels sensed by the Geiger-Mueller tubes pass a predetermined threshold. The apparatus and method are especially useful for monitoring levels of materials in hoppers, or the like, by sensing the impingement of or absence of beams of radiation on Geiger-Mueller tubes.

29 Claims, 10 Drawing Figures

APPARATUS FOR AND METHODS OF REMOTELY MONITORING OUTPUTS OF GEIGER-MUELLER TUBES

TECHNICAL FIELD

This invention relates to methods of and apparatus for remotely monitoring Geiger-Mueller tubes, and more particularly this invention relates to methods of and apparatus for remotely monitoring outputs from Geiger-Mueller tubes.

BACKGROUND AND PRIOR ART

Radiation sensors have long been relied on to determine if a hopper or vessel has been filled with material to a specified level. In a widely used approach, the sensors utilize a radiation source which produces a beam of gamma radiation at the specified level and a radiation detector, such as a Geiger-Mueller tube, which is aligned with the beam. The absence of material at the level of the beam allows relatively strong radiation flux to reach the detector while continuous presence of the product at the level of the beam attenuates the flux by an amount sufficient to interrupt detection of the beam by the Geiger-Mueller tube.

To date, the effectiveness of using Geiger-Mueller tube radiation sensors to measure material levels has been limited because, according to prior art techniques, Geiger-Mueller tubes may not be separated more than a few feet from the measurement electronics used therewith. This is because Geiger-Mueller tubes produce very fast pulse outputs having a repetition rate directly proportional to the amount of radiation sensed by the tube. If a cable is introduced between the tube and the measurement electronics, the cable will modify the pulse by both reducing the strength of the pulse and changing the shape of the pulse. The reduction in strength is a result of the cable's electrical resistance and dielectric loss while the modification of shape is due to the cable's inherent capacitance. The foregoing effects increase in magnitude with the length of the cable and interfere drastically with the operation of measurement circuits currently used. The circuitry presently used is designed to accept the very short output pulses normally associated with Geiger-Mueller tubes and will not operate with the much longer, integrated pulse which occurs at the end of a long cable run. Consequently, the electronic circuitry currently available must be located in close proximity to the tube to produce a usable output.

A primary disadvantage of having the electronic circuitry for each individual Geiger-Mueller tube in close proximity therewith is that the circuitry requires its own power supply. This disadvantage is compounded when there are a plurality of detectors using Geiger-Mueller tubes dispersed over a wide area. As is readily seen, the more detectors one has, the more expensive and cumbersome such a system may become. Power for each Geiger-Mueller tube must somehow be delivered to the site of the tube and matched with the electronics associated with the tube. In an industrial application such as monitoring material levels in vessels or hoppers, power may or may not be initially available at the sites of the vessels or hoppers or if available, the power may not be suitable for the electronics. In either case each Geiger-Mueller counter or closely associated group of Geiger-Mueller counters must have power supply facilities provided. If the power is dispensed from a central station auxiliary cables must be provided which is, of course, a relatively cumbersome and expensive approach involving many design, installation and maintenance problems. With prior art approaches amplification of and modification of the signals produced by measurement electronics at the site of measurement is necessary in order to coordinate signals from detectors with the needs of a central control. These problems have discouraged the use of radiation type level detectors for monitoring and controlling widely dispersed hopper or vessel filling operations. This has resulted in industries relying on other approaches which are either labor intensive or not otherwise entirely satisfactory because the advantages of radiation-type sensing are not utilized.

The following patents are indicative of radiation-type sensors currently available for monitoring the level of material in an enclosure of some type:

| | |
|---|---|
| 2,323,128 | Hair |
| 2,713,124 | Graham |
| 2,972,050 | Allen |
| 3,389,250 | Clemens |
| 3,560,801 | McCarther |
| 3,668,392 | Bajek et al |
| 3,944,830 | Dissing |

None of the above cited patents disclose the concept of a single panel which controls a plurality of detectors monitoring separate widely dispersed hoppers or vessels.

Considering the above listed patents individually, U.S. Pat. No. 3,389,250 discloses the use of Geiger-Mueller tubes for sensing the level of liquid in a tank, however, there is no discussion or appreciation of the concept of monitoring levels of fluid in the tank from a remote location. Furthermore, the power supply is located in proximity to the tank.

U.S. Pat. No. 2,713,124 is concerned with monitoring the level of solid material in a vessel with a Geiger-Mueller tube which is connected to a recorder spaced from the Geiger-Mueller tube by a "substantial distance." This "substantial distance" is however, only the distance from the Geiger-Mueller tube to the bottom of the tank and a preamplifier is disposed adjacent to the Geiger-Mueller tube in order to boost the signal from the tube so as to render the signal detectable by another amplifier associated with the recorder. The use of a preamplifier in proximity with each Geiger-Mueller tube decreases the practicality of using Geiger-Mueller tubes as detectors for a centrally monitored system wherein the Geiger-Mueller tubes are both dispersed and widely spaced.

U.S. Pat. No. 2,972,050 discloses a detector connected to a recorder by a relatively long cable, however, the detector is not specified as a Geiger-Mueller tube detector and an amplifier associated therewith is disclosed as being either in proximity to the detector or in proximity to the recorder. Furthermore, U.S. Pat. No. 2,972,050 does not suggest any specific arrangement for positioning the amplifier remotely from the detector and adjacent to the recorder.

U.S. Pat. Nos. 2,323,128 and 3,668,392 each disclose radiation type detectors which are connected to monitoring means by cables, however, the particular problem of having very long cables is not dealt with or discussed.

U.S. Pat. Nos. 3,560,801 and 3,944,830 are exemplary of prior art disclosures concerned with the electronics associated with radiation type detectors, however, these patents do not deal with the problems of remotely monitoring a plurality of detectors located at dispersed and distant stations.

As is readily seen by the aforementioned considerations, there is a need for some type of economical method or apparatus for remotely monitoring Geiger-Mueller tube detectors so that a plurality of these detectors can be monitored from a central station even if the detectors are widely dispersed.

OBJECTS OF THE INVENTION

It is an object of the instant invention to provide new and improved apparatus for and methods of monitoring remotely radiation type detectors.

It is a further object of the instant invention to provide new and improved apparatus for and methods of monitoring Geiger-Mueller radiation detectors.

It is a further object of the instant invention to provide new and improved apparatus for and methods of monitoring Geiger-Mueller radiation detectors wherein a plurality of detectors may be monitored at a central location.

It is a further object of the instant invention to provide new and improved apparatus for and methods of monitoring Geiger-Mueller tubes wherein the electronic circuitry associated with each tube is located at a central station rather than in close proximity to each tube.

It is a further object of the instant invention to provide new and improved methods of and apparatus for monitoring Geiger-Mueller tubes wherein no active electrical circuitry other than the tubes themselves are situated at tube locations.

It is a further object of the instant invention to provide new and improved apparatus for and methods of monitoring Geiger-Mueller tubes wherein the tubes are monitored from a distance of up to approximately 1000 feet.

It is a further object of the instant invention to provide new and improved apparatus for and methods of monitoring Geiger-Mueller detectors wherein the electronics associated with each detector is located at a central station and wherein the electronics utilize a commercially available integrated circuit as a component thereof so that critical functions of the system may be contained within one integrated circuit package.

It is a further object of the instant invention to provide new and improved apparatus for and methods of monitoring a plurality of hoppers or vessels disposed at widely dispersed locations wherein the methods and apparatus utilize Geiger-Mueller tubes.

SUMMARY OF THE INVENTION

In order to accomplish the aforementioned objects, the instant invention contemplates a Geiger-Mueller tube detection system wherein an individual Geiger-Mueller tube is connected to a monitoring station via a cable through electronic circuitry located at the monitoring station. More specifically, the signal received by the electronic circuit is fed to a charge pump so as to be converted from a frequency analog to a voltage analog. The charge pump charges a capacitor in proportion to the frequency of the signal it receives from the cable so that the size of the charge on the capacitor depends on the amount of the radiation flux at the detector. The charge on the capacitor is then compared to a selected voltage and an output occurs when the selected voltage is exceeded. The output is then used for any desired function of the monitor such as, for example, triggering an alarm.

The instant invention further contemplates utilizing a plurality of Geiger-Mueller tubes at a plurality of dispersed locations and confining the electronics associated with each Geiger-Mueller tube to a central monitoring station.

A particular advantage of the monitoring circuit in accordance with the invention is the fact that signals from a Geiger-Mueller tube may be received and processed using relatively long cables without using any active elements such as signal preamplifiers near the GM tube itself. In fact, there are no active components positioned at the cable end connected to the GM tube. The monitoring circuit, in accordance with the invention, is extremely sensitive to relatively low amplitude long pulse width signals which result from the use of long cables, e.g., over ten feet in length. Typical signal receiving and processing electronics utilized in conventional prior art devices is sensitive to narrow high amplitude pulses coming from the GM tube without substantial attenuation by the signal cable, e.g., signals having a pulse heighth of nominally 50 volts and a pulse width on the order of 200 microseconds. Utilizing the apparatus in accordance with the invention, the output of the GM tube may be transmitted to a remote monitoring site (ten feet or more away, for example) and still process even though the pulse attenuation, due to cable loss, is substantial, a capability heretofore not present in existing GM detecting/monitoring systems. The apparatus of the invention is sensitive to detect input signal levels having an extremely low amplitude on the order of 250 milivolts or more, and a relatively wide pulse width on the order of one millisecond, which allows utilization of the system with cable lengths in the range of 10 to 1,000 feet. The electronics utilized in the instant invention is particularly sensitive to pulses transmitted with substantial attenuation and thus is particularly adapted for use in long length cable monitoring systems.

DETAILED DESCRIPTION OF THE PREFERRED EMBODIMENTS

Figure 1:
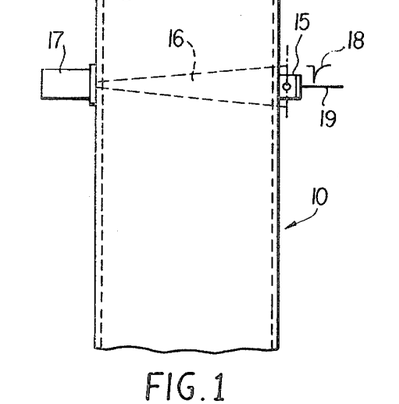
FIG. 1 is a schematic cross-sectional view showing a first embodiment of a Geiger-Mueller detector installed on a hopper or vessel for detecting the level of material in the hopper or vessel.
Figure 2:
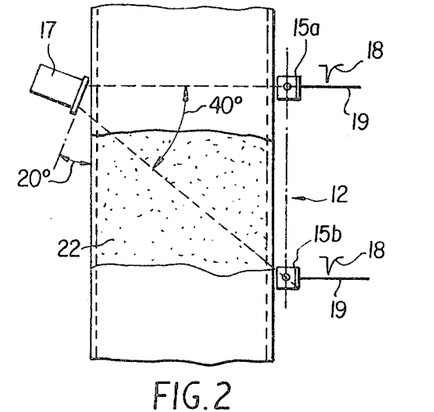
FIG. 2 is a schematic cross-sectional view of a second embodiment of a Geiger-Mueller detector installation on a hopper or vessel in order to detect the level of a material within the hopper or vessel.
Figure 3:
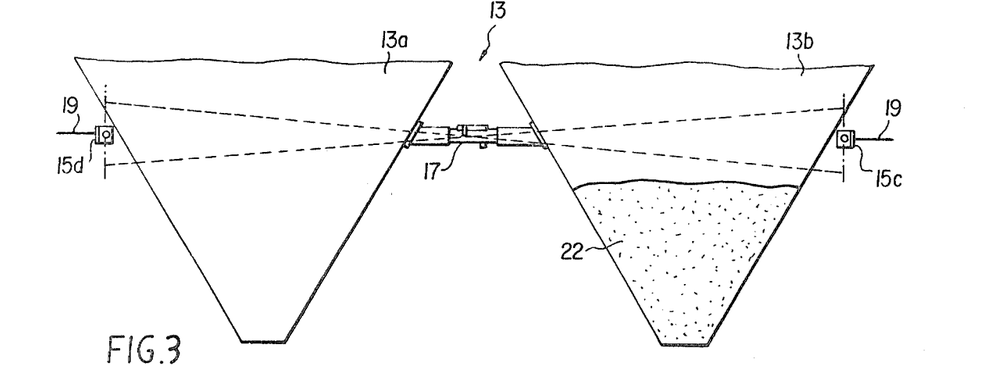
FIG. 3 is a schematic cross-sectional view of a third embodiment of a Geiger-Mueller installation wherein a pair of adjacent vessels or hoppers are monitored by a Geiger-Mueller tube to determine the level of material within the vessels or hoppers.

Referring now to FIGS. 1, 2 and 3, there are shown three embodiments of Geiger-Mueller tube installations on hoppers or vessels 10, 12 and 13, respectively. In each case, a Geiger-Mueller tube 15 is disposed outside of the hopper or vessel and detects a highly collimated radiation beam 16 emitted by a radiation source 17. Impingement of the radiation beams on the tube 15 causes ionization of a gas in the tube resulting in discharges across the tube. These discharges generate pulses 18 which are impressed on the central conductor of a coaxial cable 19. The embodiments of FIGS. 1-3 show various installations for a single detector 15 installed outside of a hopper or vessel 10. Each of these installations operates essentially in the same manner wherein when material 22 is present between the source 17 and Geiger-Mueller tube 15 the level of radiation detected by the detector 15 drops to background level due to attenuation of the radiation beam by the material. The presence or absence of pulses 18 in the coaxial cable 19 is indicative of the absence or presence of material at the level of the radiation beam 16.

Figure 4:
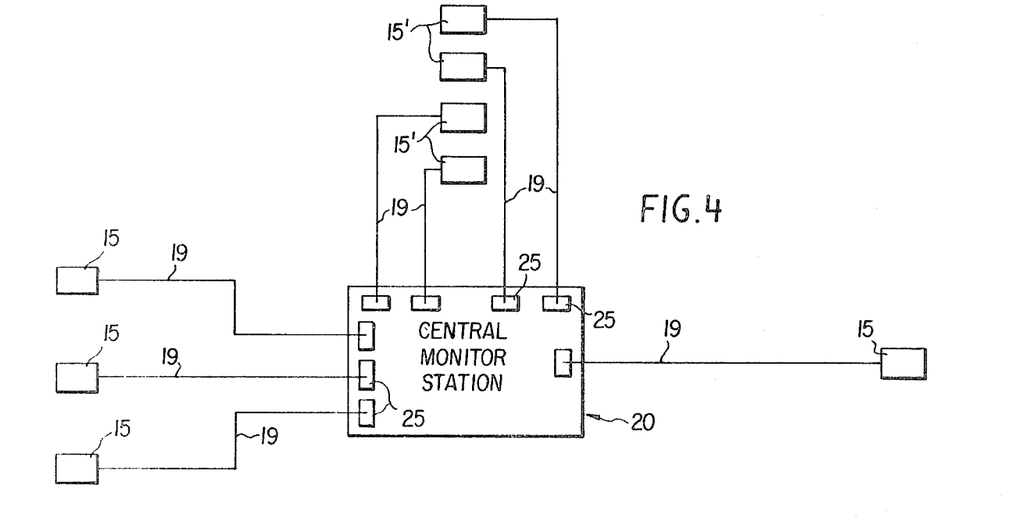
FIG. 4 is a block diagram showing a plurality of Geiger-Mueller tubes connected to a central monitoring station with the measurement electronics for each tube located at the central station.

Referring now to FIG. 4, a plurality of Geiger-Mueller tubes 15 are connected via coaxial cables 19 to a central monitoring station 20. The cables 19 may be up to 1000 feet in length and may be connected to dispersed Geiger-Mueller tubes 15 or to Geiger-Mueller tubes 15' which are located near to one another but are perhaps remote from central monitoring station 20. A separate alarm module 25 including the measurement electronics for a single Geiger-Mueller tube 15 is connected to each tube and located in the central monitoring station 20.

Figures 5, 9:
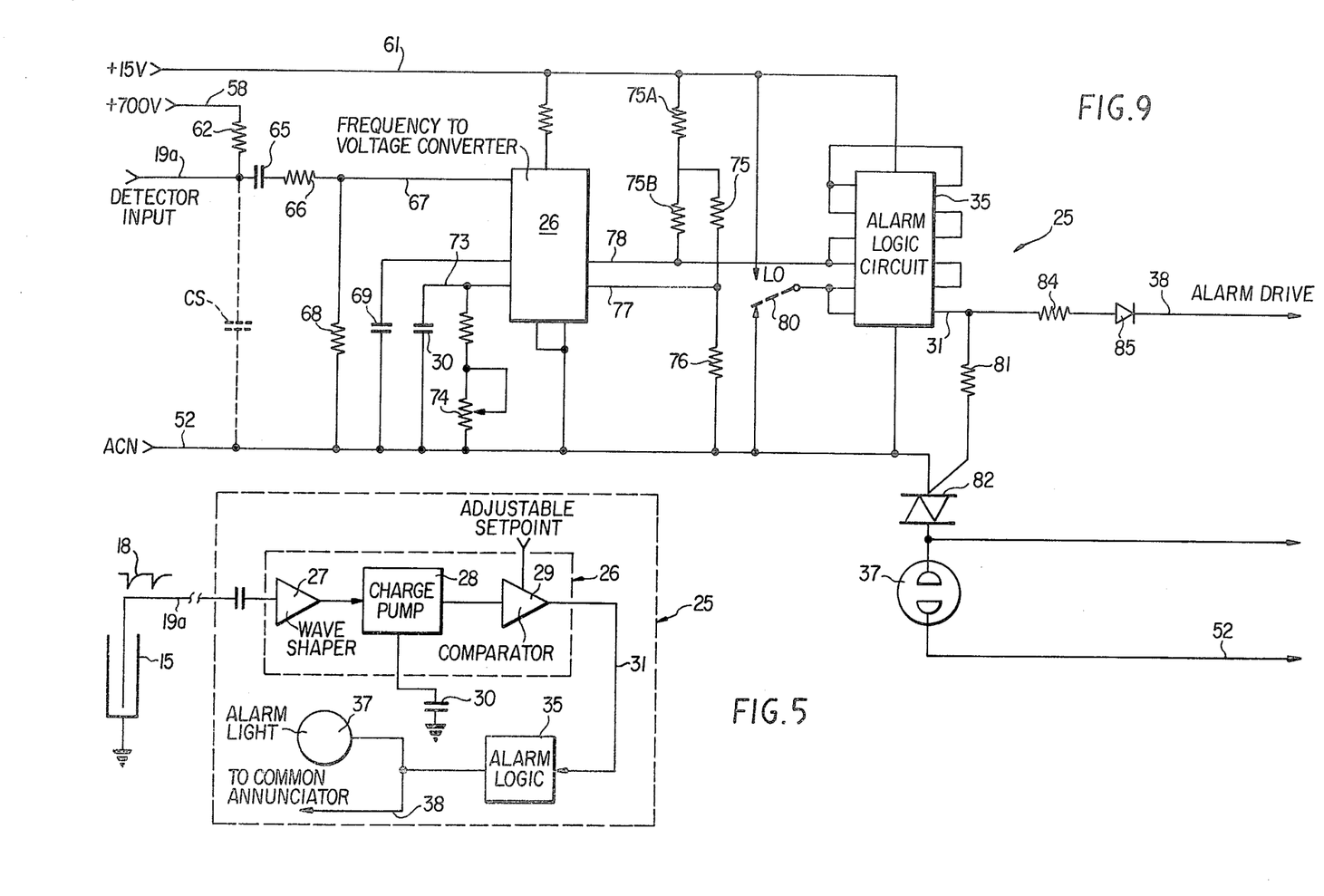
FIG. 5 is a schematic diagram of a monitoring circuit for monitoring a single Geiger-Mueller tube disposed at a remote location.
FIG. 9 is a more detailed circuit diagram of the electronic circuit shown in FIG. 5 and associated with each Geiger-Mueller tube but located within the central monitoring station of FIGS. 4, 6 and 7.

A general circuit diagram of an individual alarm module 25 is shown in FIG. 5 while a more detailed circuit diagram of the alarm module is illustrated by FIG. 9. As is seen in FIG. 5, a single Geiger-Mueller tube 15 is connected to a frequency to voltage converter circuit chip 26 which includes waveshaping circuitry 27, a charge pump 28 and a comparator 29. The waveshaping circuitry 27 increases the amplitude of and cleans-up the pulses 18 received from the center conductor 19a of coaxial cable 19. The thus modified pulses are applied to the charge pump 28 which converts the signal from a frequency analog to a voltage analog. The charge pump 28 charges a capacitor 30 in proportion to the frequency of the signal it receives from the waveshaping circuit 27. The charge on the capacitor 30 is thus proportional to and indicative of the strength of the radiation field detected by the Geiger-Mueller tube 15. The comparator 29 is selected to provide a set point voltage and an output is produced over line 31 when that set point is exceeded. Accordingly, there will be a larger voltage stored by the capacitor 30 during a predetermined time interval if there are many pulses 18 impressed on the cable 19 by the Geiger-Mueller tube 15 than if there are few pulses impressed on the cable.

When the radiation beam 16 (FIGS. 1-3) is not attenuated by the presence of material 22 between the Geiger-Mueller tube 15 and radiation source 17, there will be a relatively large number of pulses 18 on the caoxial cable 19; however, when the material is disposed between the radiation source and the Geiger-Mueller tube 15, the radiation beam will be attenuated and there will be relatively few pulses impressed on the coaxial cable. If there is material 22 interrupting the radiation beam 16, then there is no output on the line 31 (FIG. 5) because the set point is not exceeded; however, if there is no material interrupting the radiation beam then there is an output on line 31 because the set point is exceeded.

When there is a signal on line 31, the signal is applied to an alarm logic circuit 35 which is wired selectively either to trigger an alarm when there is a full vessel or to trigger an alarm when there is an empty vessel. The condition which triggers the alarm depends on which condition one desires to detect. The alarm logic circuit 35 is in turn connected to a specific alarm lamp 37 which indicates the condition of the single Geiger-Mueller tube 15 connected to the alarm module 25. A line 38 connects the alarm logic circuit 35 and annunciator (see 46 and 96 of FIGS. 6 and 8) which are activated if any one of the Geiger-Mueller tubes 15 in the entire system, as illustrated by FIG. 4, detects an alarm condition.

Figure 6:
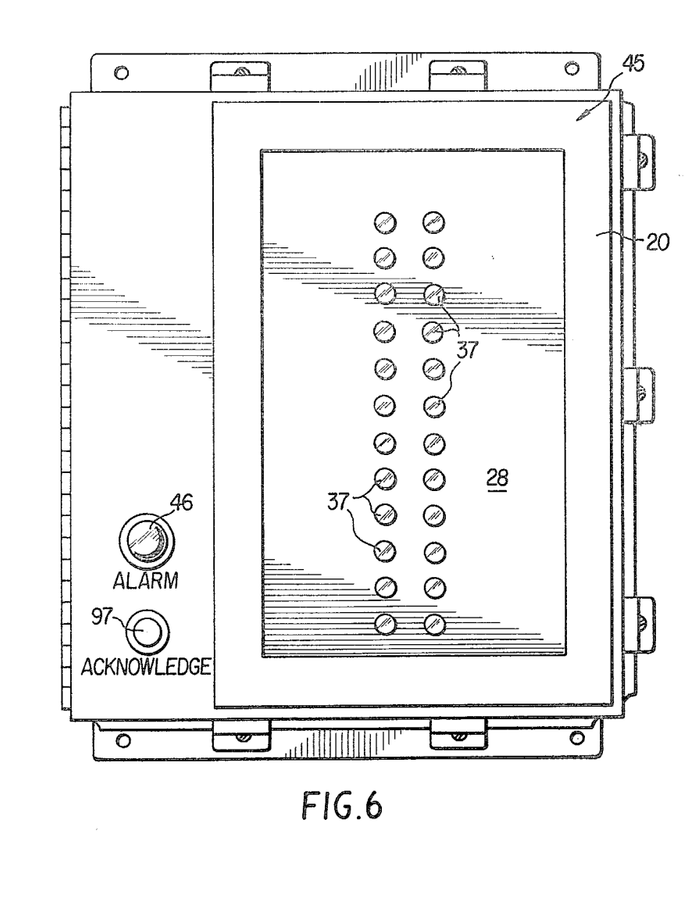
FIG. 6 is a front view of a control panel of the central monitoring station of FIG. 4.
Figure 7:
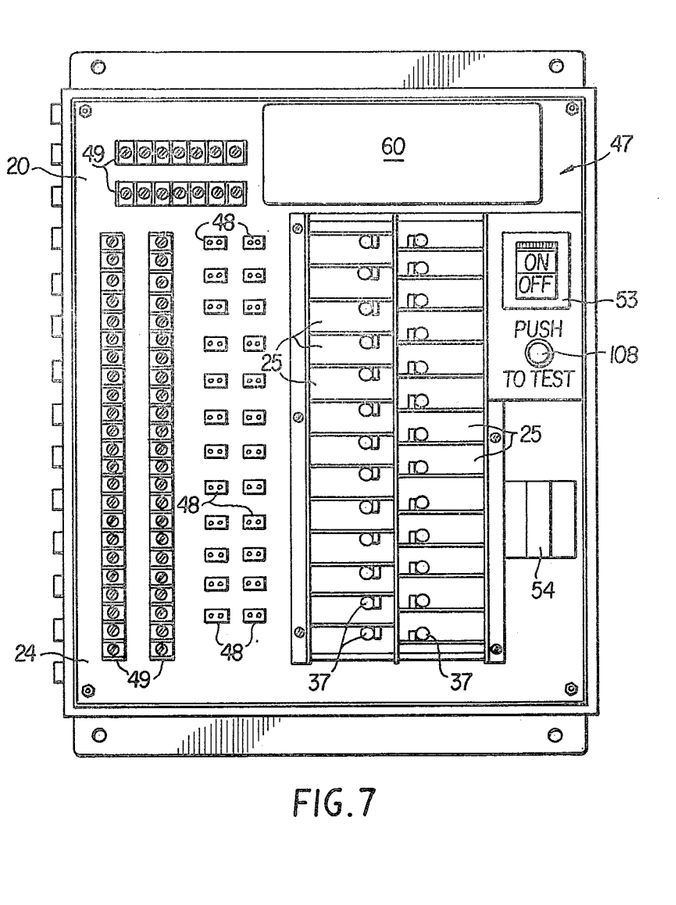
FIG. 7 is a back view of the central panel of the central monitoring station of FIGS. 4 and 6.

Referring now to FIG. 6, it is seen that the central control monitor 20 has a front panel 45 through which the individual alarm lamps 37 are displayed. The panel 45 is preferably a hinged door. The panel 45 also includes a general alarm lamp 46 which is connected by lines to each of the lines 38 (see FIG. 5) extending from the individual alarm modules 25. Referring now to FIG. 7, the rear side 47 of the central control monitor 20 includes a bank of electrical connectors 48 to which individual coaxial cables 19 are connected. Each of the connectors 48 is connected to a separate alarm module 25. Also associated with each module 25 and with each connector 48 are terminal strips 49 which are used to wire the various circuits in the central control monitor together and to line current.

Figures 8, 10:
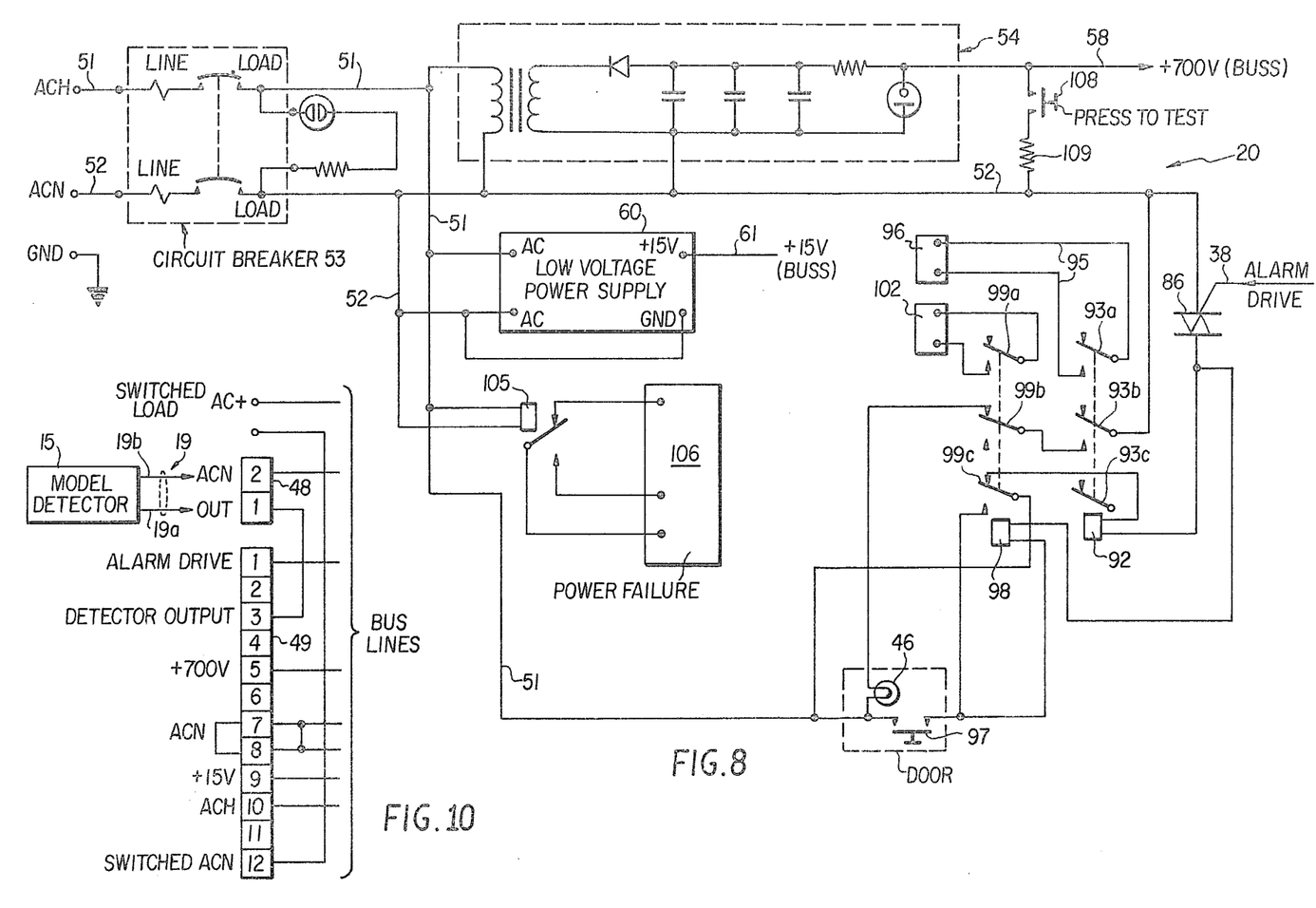
FIG. 8 is a circuit for general operation of the monitor shown in FIG. 5.
FIG. 10 is a circuit diagram showing a terminal block interconnecting the circuits of FIGS. 8 and 9 and providing power inputs to the circuits.

Referring now to FIGS. 8 and 10 in conjunction with FIGS. 6 and 7 as well as FIG. 9, line voltage is introduced to the central control module 20 over AC lines 51 (ACH-hot line) and 52 (ACN-neutral) through a circuit breaker 53. Lines 51 and 52 are applied to a high voltage power rectifier supply 54 so as to produce a 700 volt DC potential on a bus 58. The bus 58 is connected to each of the alarm modules 25 and, through a 2.7 M resistor 62 therein, applies a bias to the central conductor 19a of the coaxial cable 19. The biasing connection is effected by one pole of a connector 48, the other pole of the connector connecting the outer sheath 19b of the coaxial cable 19 to ground through one of the terminal strips 49 (FIG. 6).

The AC lines 51 and 52, respectively, are also connected to a low voltage power supply 60 as, for example, Electrostatic Part No. 30-15. The low voltage power supply 60 impresses a 15 volt DC output over bus 61 which is connected to each of the alarm modules 25. The low voltage line 61 in each of the alarm modules 25 applies 15 volts to both the frequency to voltage converter chip 26 (also see FIG. 5) and the logic chip 35 (also see FIG. 5) in the alarm module 25.

The AC neutral line 52 serves as a signal ground for operation of chips 26 and 35 as shown in the circuit of FIG. 9. When using relatively short lengths of coaxial cable, a capacitor CS, for example, 0.4 uf, 1 Kv, may be positioned between the ACN line 52 and the connection between the 700 volt DC bus 58 and the detector input which is the central conductor 19a in order to cause the Geiger-Mueller tube 15 attached to the central conductor to fire. In operation, when a photon strikes the Geiger-Mueller tube 15, ionization of the gas inside the tube occurs causing current to be drawn from the 700 DC voltage on line 58 to the 2.7 M resistor 62 causing a voltage drop across resistor 62 which appears as a negative going pulse. This pulse is coupled across a capacitor 65 (1200 pF) and a current limiting resistor 66 to an input 67 of the frequency to voltage converter chip 26. A 470K resistor 68 acts as a pull down resistor to prevent noise from entering the frequency to voltage converter chip 26 in the absence of pulses from the Geiger-Mueller tube 15. The chip 26 may be obtained, for example, from Kay-Ray, Inc., Arlington Heights, Ill., part No. 440-002907 or from National Semiconductor as part #LM2907.

The chip 26 produces a constant amplitude, constant width pulse in response to pulses applied thereto from input 67. A capacitor 69 determines the width of the constant amplitude, constant width pulses and the constant width pulses are used to apply a charge over line 73 to the capacitor 30 (see FIG. 5). The charge on the capacitor 30 is directly proportional to the number of pulses received from the Geiger-Mueller tube 15 during a given period of time and is therefore proportional to the strength of the radiation field sensed by the Geiger-Mueller tube. A potentiometer 74 provides for limited adjustment of the rate that charge is accumulated by the capacitor 30 so as to insure that the charge is analogous to pulse frequency. Additional internal circuitry in the chip 26 compares the voltage built up on capacitor 30 with a reference voltage determined by two resistors 75 and 76 which is applied to the chip 26 over line 77. When the voltage on capacitor 30 exceeds the voltage on line 77 an output is produced on line 78. Resistors 75 and 76 combine with resistors 75A and 75B to provide controlled hysteresis for the switching action so that when radiation is in transition from a low radiation or background condition (approximately 0.2 mR/hr.) switching action will occur with approximately 7.5 volts DC occurring on line 73. As the radiation field returns to background level switching will not occur until the voltage on line 73 is lower than approximately 4.5 volts DC. The controlled hysteresis prevents false triggering caused by the varying nature of the radiation field detected by the Geiger-Mueller tubes 15.

The output of frequency to voltage converter chip 26 is directly coupled over line 78 to the alarm logic circuit chip 35 (also see FIG. 5) which is a standard logic gate such as model No. MM74 COO, that can be programmed by a mode jumper 80. If the jumper 80 is wired to connect the low voltage DC from line 61 to the alarm logic circuit chip 35 then chip 35 triggers an alarm when there is an output by chip 26 over line 78. When the jumper 80 is wired to connect the line 52 to chip 35 there will be an output from the chip 35 when there is no output from the chip 26 on line 78. By using this arrangement, an alarm condition can be provided either when there is a high product level with no radiation received by the Geiger-Mueller tube 15 or a low product level when there is radiation received by the Geiger-Mueller tube. When there is an output by the alarm logic circuit chip 35, current is applied over line 31 through a resistor 81 to the gate of a triac 82 to illuminate the single alarm light 37 of the particular alarm module 25. Current is also applied over line 38 (also see FIG. 5) through resistor 84 and diode 85 to the common or general alarm light 46 and an audio alarm (see FIGS. 6 and 8).

Referring now to FIG. 8, the line 38 applies the alarm signal to triac 86 which is also connected to the AC lines 51 and 52. Upon activating the triac 86 with an alarm signal over line 38 an alarm relay 92 is operated to close switches 93a–93c. When switch 93b is closed it connects the AC line 52 to the general alarm lamp 46 which is already connected to AC line 51 so as to light the lamp 46 and alert personnel that there is an alarm condition at one of the hoppers or vessels (see FIGS. 1–4) being monitored. When the switch 93a is closed a circuit is established in line 95 which may be connected to an auxiliary alarm device such as an audible alarm 96.

When the operator wishes to shut the alarm 96 off, he closes a pushbutton 97 which operates a relay 98 that opens switch 99b thereby extinguishing lamp 46 and de-energizing relay 92 by opening switch 99c. Relay 92 then returns contacts 93a, 93b and 93c to their initial position deactivating the audio alarm 96 and opening the circuit to the general alarm lamp 46. In addition, operation of the pushbutton switch 97 closes switch 99a to signal an alarm acknowledged indicator 102 that an alarm condition still exists but has been acknowledged by the operator. The indicator 102 will display an alarm condition until the cause for the alarm condition has been rectified or the alarm modules 25 removed.

The central control module 20 also includes safety features such as relay 105 which is connected to the AC lines 51 and 52 so as to provide a single pole, double throw indication, via contacts 106, that power is being applied to the system as a whole. As pointed out previously, power on lines 51 and 52 is controlled by a circuit breaker 53 and as seen in FIG. 7 both the high voltage power supply 54 and the low voltage power supply 55 are contained within the enclosure of the central control monitor 20.

In order to test the system a pushbutton 108 is provided, which when pushed removes the high voltage potential from the Geiger-Mueller tubes 15 by connecting the 700 volt line 58 to the AC line 52 through 10 K resistor 109. Removal of the high potential voltage from the Geiger-Mueller tubes 15 prevents the tubes from producing an output or simulates a high product level condition for system test purposes.

Although the aforedescribed apparatus and method is used in a preferred embodiment to monitor the level of material 22 in vessels, hoppers or other containers, the system may have other applications such as monitoring the height of material in a well or borehole. The entire apparatus or subsystems thereof and methods of using the apparatus and subsystem therein may be used for any application wherein the outputs of Geiger-Mueller tubes are monitored and are limited only by the following claims.

What is claimed is:

1. A method of measuring the output of at least one Geiger-Mueller tube remotely located from a monitoring station comprising the steps of:
   (a) transmitting the output of the Geiger-Mueller tube over a cable attached thereto to the monitoring station without amplification of the signal prior to transmitting;
   (b) converting output pulses as received at the monitoring station from the remote Geiger-Mueller tube to a voltage signal proportional to the frequency of the output pulse;

(c) comparing the voltage signal to a reference voltage signal;

(d) producing a trigger signal when the magnitude of the voltage signal approaches and passes the reference voltage; and (e) triggering a specific indicator with the trigger signal to indicate the occurrence of the trigger signal.

2. The method of claim 1 wherein the signal is transmitted a distance of up to approximately one thousand feet.

3. The method of claim 2 wherein there are a plurality of Geiger-Mueller tubes and wherein steps (a), (b), (c), (d) and (e) are performed individually for each Geiger-Mueller tube.

4. The method of claim 3 further including the step of:

(f) triggering a general indicator when any of the Geiger-Mueller tubes trigger a specific indicator according to step (e).

5. The method of claim 4 further including the steps of: '(g) terminating operation of the general indicator while maintaining operation of the specific indicator to acknowledge the existence of the trigger signal.

6. The method of claims 1, 2, 3, 4 or 5 wherein in step (d) triggering occurs when the voltage signal exceeds the reference voltage.

7. The method of claims 1, 2, 3, 4 or 5 wherein in step (d) triggering occurs when the voltage signal becomes less than the reference voltage.

8. Apparatus for monitoring radiation flux comprising:

at least one Geiger-Mueller tube having an output which is a series of pulses having a frequency which increases with increases in radiation flux;

a remote monitor for monitoring the radiation flux;

a cable connected to the Geiger-Mueller tube for transmitting the pulses to the remote monitor without amplifying the pulses prior to transmitting;

an electronics module connected to the cable only at the remote monitor for receiving and monitoring the pulses, wherein the electronics module comprises:

a power supply connected to provide a voltage to the Geiger-Mueller tube along said cable, said pulses comprising negative going pulses causing a drop in power supply voltage on said cable;

means for converting the pulse frequency to a voltage proportional to the pulse frequency;

means for comparing the converted voltage to a threshold voltage level which is proportional to a selected level of radiation flux; and output means for outputting when the converted voltage exceeds the threshold voltage thereby providing an indication that the level of radiation flux has increased beyond the selected level.

9. The apparatus of claim 8 wherein there are a plurality of Geiger-Mueller tubes each having a separate cable for connection to an electronics module at the remote monitor.

10. The apparatus of claim 8 further comprising:

specific indicating means connected to the output means for indicating the level of radiation flux;

mode selection means connecting the indicating means to the output means for selecting between activating the indicating means when the converted voltage exceeds the threshold voltage and activating the indicating means when the converted voltage is less than the threshold voltage.

11. The apparatus of claim 10 wherein there are a plurality of Geiger-Mueller tubes each having a separate cable for connection to an electronics module at the remote monitor and when the remote monitor is a unit at a central location.

12. The apparatus of claim 11 further comprising:

a bus in the remote monitor connecting each electronics module to a general indicator via the mode selection means for activating the general indicator when any of the specific indicating means are activated by the mode selection means.

13. The apparatus of claim 12 further comprising:

means connected to the general indicator for deactivating the general indicator while the operation of the specific indicator is maintained.

14. The apparatus of claim 8, 9, 10, 11, 12 or 13 wherein any cables therein recited have a length of up to approximately one thousand feet.

15. Apparatus for measuring the output of at least one Geieger-Mueller tube remote from a monitoring station comprising:

(a) means for connecting an output of said remote Geiger-Mueller tube to one end of a cable, therebeing no interposing electronic circuitry to amplify the output between the cable and Geiger-Mueller tube;

(b) means for connecting the other end of said cable to said monitoring station, said monitoring station including:

(i) means for converting output pulses from said remote Geiger-Mueller tube to a voltage signal proportional to the frequency of said output pulses;

(ii) means for comparing said voltage signal to a reference voltage signal, and for providing a trigger signal if said voltage signal exceeds said reference voltage; and (iii) indicating means for receiving said trigger signal for indicating occurrence of same.

16. The apparatus of claim 15 wherein there are a plurality of remote Geiger-Mueller tubes connected to the monitoring station and wherein for each Geiger-Mueller tube there are means (i), (ii) and (iii) located at the monitoring station.

17. The apparatus of claim 16 wherein the cables are up to approximately one thousand feet long.

18. The apparatus of claim 17 wherein the monitoring station further comprises:

power supplies for supplying power to the means (i), (ii) and (iii) and for supplying voltage to the cables.

19. The apparatus of claim 18 wherein the monitoring station further comprises:

general indicating means connected to each indication means for displaying a signal when there is an occurrence of a trigger signal.

20. The apparatus of claim 19 wherein the monitoring station further comprises:

acknowledgement means connected to the general indicating means for terminating operation thereof without interrupting operation of the indicating means associated with each Geiger-Mueller tube.

21. An apparatus for monitoring at least one enclosure for determining the presence or absence of material in at least one location within the enclosure comprising:

radiation source means proximate the enclosure for emitting radiation into the enclosure;

Geiger-Mueller tube means, positioned proximate the enclosure and spaced from the source means, the Geiger-Mueller tube means providing electrical pulses at a relatively high frequency when material is absent between the radiation source means and Geiger-Mueller tube means and emitting electrical pulses at a relatively low frequency when there is material present between the radiation source means and Geiger-Mueller tube means;

cable means having a first end and a remote second end which is not adjacent to the Geiger-Mueller tube means, said first end being connected to the Geiger-Mueller tube means for transmitting the electrical pulses without amplification;

an electronics module connected to the remote second end of the cable means for detecting the electrical pulses, the electronics module comprising:

means for converting the pulse frequency to a signal voltage proportional to the pulse frequency;

means for comparing the signal voltage to a threshold voltage level which is proportional to the frequency of pulses emitted by the Geiger-Mueller tube means when there is material present between the Geiger-Mueller tube means and radiation source means; and means for providing an output when the signal voltage exceeds the threshold voltage thereby providing an indication that material is absent between the Geiger-Mueller tube means and radiation source means.

22. The apparatus of claim 21 wherein the electronics module further comprises:

specific indicating means connected to the output means for indicating the presence or absence of material;

mode selection means connecting the indicating means to the output means for selecting between activating the specific indicating means when the signal voltage exceeds the threshold voltage and activating the specific indicating means when the signal voltage is less than the threshold voltage to indicate the absence or presence of material, respectively.

23. The apparatus of claim 21 wherein there are a plurality of enclosures each having at least one Geiger-Mueller tube means, wherein the cable means comprises a separate cable connected to each Geiger-Mueller tube means and wherein the apparatus further comprises a remote monitor at a central location which includes a separate electronics module attached to each cable.

24. The apparatus of claim 23 wherein each electronics module further comprises:

specific indicating means connected to the output means for indicating the presence or absence of material;

mode selection means connecting the indicating means to the output means for selecting between activating the specific indicating means when the signal voltage exceeds the threshold voltage and activating the specific indicating means when the signal voltage is less than the threshold voltage to indicate the absence or presence of material, respectively.

25. The apparatus of claim 24 further comprising:

a bus in the remote monitor connecting each electronics module to a general indicator via the mode selection means for activating the general indicator when any of the specific indicating means are activated by the mode selection means.

26. The apparatus of claim 25 further comprising:

means connected to the general indicator for deactivating the general indicator while the operation of the specific indicator is maintained.

27. The apparatus of claim 21, 22, 23, 24, 25 or 26 wherein any cables therein recited have a length of up to approximately one thousand feet.

28. A method as recited in claim 1 wherein the step of transmitting comprises transmitting the Geiger-Mueller tube output over a cable having a length between approximately 10 and 1,000 feet.

29. The apparatus of claim 8, 9, 10, 11, 12 or 13 wherein any cables therein recited have a length between approximately 10 and 1,000 feet.

* * * * *